United States Patent [19]

Stoyan

[11] 4,158,030
[45] Jun. 12, 1979

[54] METHOD FOR MAKING LENSES FROM A MODIFIED POLYMERIZATION PRODUCT OF METHYL METHACRYLATE

[76] Inventor: Nick Stoyan, 4505 Van Nuys Blvd., Sherman Oaks, Calif. 91413

[21] Appl. No.: 809,557

[22] Filed: Jun. 24, 1977

[51] Int. Cl.² .................................................. B29D 11/00
[52] U.S. Cl. .................................................. 264/1; 3/13;
    264/342 RE; 351/160 H
[58] Field of Search ............... 264/1, 2, 342 RE, 230;
    351/159, 160, 177; 350/175 NG; 3/13

[56] References Cited

U.S. PATENT DOCUMENTS

| | | | |
|---|---|---|---|
| 2,302,918 | 11/1942 | Smith | 264/1 |
| 3,647,736 | 3/1972 | Ewell | 264/1 |
| 3,651,192 | 3/1972 | Erickson | 264/1 |
| 3,807,398 | 4/1974 | Grucza | 264/1 |
| 3,839,304 | 10/1974 | Hovey | 264/1 |
| 3,841,985 | 10/1974 | O'Driscoll et al. | 264/1 |
| 3,966,847 | 6/1976 | Seiderman | 351/160 |
| 3,978,164 | 8/1976 | Le Boeuf et al. | 264/1 |

*Primary Examiner*—James B. Lowe
*Attorney, Agent, or Firm*—Huebner & Worrel

[57] ABSTRACT

The method of making lenses for the eyes from an improved modified polymerization product of methyl methacrylate. The product is in the as-cast form from which satisfactory lenses can be made, but is improved in optical clarity and wetability by heat treating and shrinking the product in a linear direction and thickening the product in another direction prior to cutting the product for making the lenses. After cooling the lens blanks are cut and the lenses are made by conventional grinding.

1 Claim, 5 Drawing Figures

METHOD FOR MAKING LENSES FROM A MODIFIED POLYMERIZATION PRODUCT OF METHYL METHACRYLATE

BACKGROUND OF THE INVENTION

Heretofore in the production of contact lens or implanted lens a polymerization product of acrylic acid, which includes both modified and unmodified acrylics has been used.

While such acrylics have been found to possess wetting qualities and to some extent ease of tear transport when formed into contact lens, these qualities have not been uniform. Additionally, the previous acrylics in optical testing have been found to lack clarity and sharpness requiring a thicker finished lens to achieve the proper optics desired.

SUMMARY OF THE INVENTION

The invention includes the use of pre-shrunk acrylics preferably of the modified polymerization products of methyl methacrylate in the formation of lens blanks. One form of such pre-shrunk acrylic plastic is a product manufactured by Rohm and Haas and identified as "Plexiglas® 11UVA". This particular plastic also possesses ultra-violet absorbing qualities so that contact lens formed therefrom will not allow ultra-violet rays to penetrate the cornea.

By the utilization of pre-shrunk acrylics the optical effect is greatly increased due to structural change and thus thinner contact lens or implants can be produced. Such thinness is of course much better for the lens wearer and wearing time can usually be increased.

Further, lenses formed from pre-shrunk acrylics have an increased uniformity of wetness which result in more comfort for the lens wearer.

Additionally, the pre-shrunk acrylics when formed into completed contact lenses possess a flexibility which again results in greater comfort to the wearer, by the lens acting as a pump when blinking occurs which in turn allows greater oxygen to contact the cornea of the eye.

Another object is to utilize pre-shrunk acrylic which when cut into blanks and formed into finished lenses can be dyed or tinted for cosmetic color effect or ease of identification when lost.

These and other objects and advantages will become apparent from the following description and drawings wherein:

DETAILED DESCRIPTION OF THE PREFERRED EMBODIMENT

Figure 1:
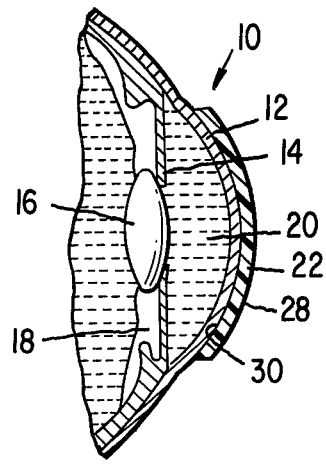
FIG. 1 is a cross-sectional environmental view showing a contact lens of the present invention in position on the cornea of an eye.
Figure 2:
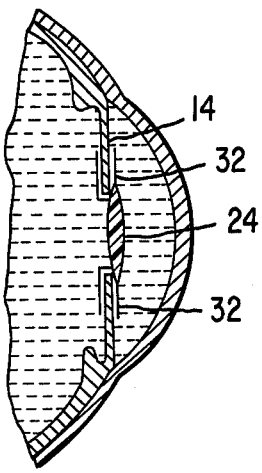
FIG. 2 is a cross-sectional view of an eye with a Binkhorst iris clip type lens which can be made from the present invention.
Figure 3:
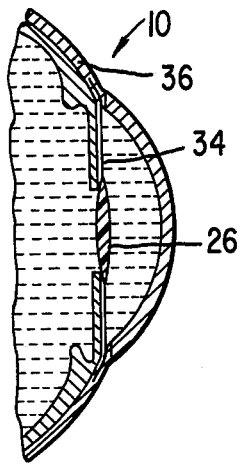
FIG. 3 is a cross-sectional view of an eye with a lens implant which can be made from the present invention.

The drawings of FIGS. 1, 2 and 3 disclose cross-sectional views of the frontal portion of a human eye generally designated 10. In FIG. 1 there is shown a cornea 12, iris 14 and natural lens 16 suspended between the suspensory ligament 18. Between the cornea 12 and lens 16 is the anterior aqueous chamber 20.

In FIGS. 2 and 3 the natural lens 16 has been removed and an appropriate implanted lens affixed.

Each of the first three figures illustrate a form of manufactured lenses made according to the methods of the present invention. While the invention does not reside in the end finish lens configuration, the lens such as a cornea contact lens 22 is illustrated as it is positioned against the cornea 12 in FIG. 1. In FIG. 2 there is illustrated an implant lens 24 which is known as the "Blinkhorst iris clip lens". In FIG. 3 there is illustrated an implant lens 26 referred to as using external fixation as developed by Dr. Strampelli of Italy.

The lens 22 in FIG. 1 has a convex outer surface 28 and a concave inner surface 30.

With regard to lens 24, the natural eye lens 16 has been removed and the lens 24 containing clips 32 is implanted whereby the clips 32 can engage both sides of the iris 14.

In FIG. 3 the lens 26 includes a continuous loop 34 which has the lens 26 suspended therebetween and the loop 34 is affixed to the conjunctiva 36 of the eye 10.

The true purpose of illustrating the various lens in situ in FIGS. 1 through 3 is to show that artificial lens such as 22, 24 and 26 can be formed from acrylic plastic which has been pre-shrunk.

Figure 4:
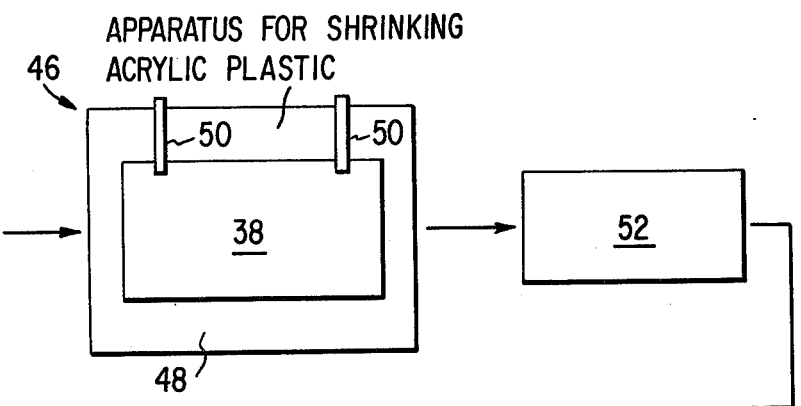
FIG. 4 is step diagram of the method of producing a contact lens or implant lens of the present invention.

FIG. 4 illustrates steps utilized in commencing with a plastic sheet 38 through various stages to a complete manufactured lens 40 be it a corneal type 22, or implants as 24 and 26.

Generally the plastic sheet 38 for best results, is an acrylic such as polymerization products of acrylic acid. Especially good for prior lens are modified polymerization products of methyl methacrylate. Such plastic is normally found to have an Index of Refraction of 1.49.

While the aforementioned plastic in its as-cast form has proven satisfactory for manufactured optical lenses 40 the pre-shrinking of the material prior to forming lens blanks 44 has been found to produce a finished manufactured optical lens 40 of much superior characteristics.

The pre-shrinking step 46 of FIG. 4 is accomplished by placing the plastic sheet 38 as cast into a conventional oven 48 and suspending the same by brackets 50 or other convenient means. The oven 48 is then heated to approximately 137.7° C. (280° F.) and the sheet is maintained at that temperature for approximately 30 minutes. This temperature is just below the normal hot forming temperature for such plastic so that its shape can be maintained. At the conclusion of that time the temperature is reduced to approximately room temperature and the sheet 52 which is pre-annealed or shrunk is removed.

By such heating technique, the as-cast sheet 38 has been shrunk by approximately 2% from its original linear dimension and increased in thickness by approximately 4% to form pre-shrunk sheet 52. By this shrinking the molecular structure of sheet 52 has been compressed because of the shrinking. This provides a plastic of exceptional optical clarity wherein the stresses are relieved. Further, such treatment has increased the wetting quality of the finished lens 40. Such wetting capabilities increase the ease of tear transport between the concave surface 30 of the lens 22 and the cornea 12 which in turn allows less frictional resistance increasing the comfort to the lens wearer.

After the plastic is pre-shrunk, FIG. 4, to sheet 52 and then cut into blanks 44, the lenses 40 can be made by appropriate and conventional grinding steps 54.

While the steps of FIG. 4 show the resultant lens 40 as the contact cornea type such as seen in FIG. 1, the blank 44 can be finished into any appropriate lens such as the implants 24 and 26 of FIGS. 2 and 3.

In order to form blanks 44, the sheet 52 may be die cut or otherwise cut to produce buttons or blanks 44.

Figure 5:
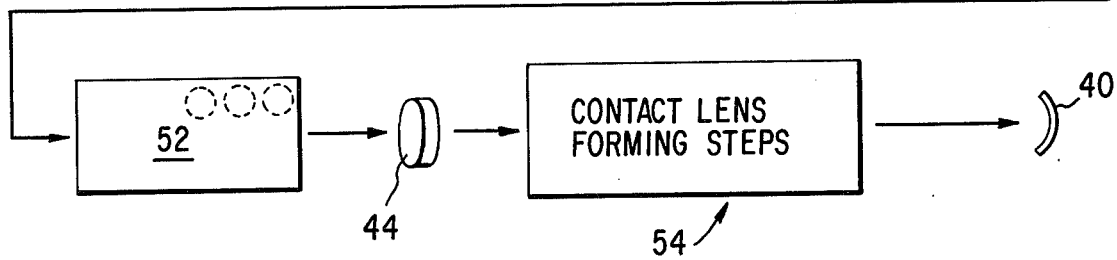
FIG. 5 is a modified shape of material from which lenses of the present invention may be produced.
Figure 5:
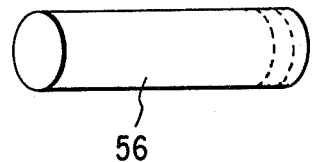

In FIG. 5 there is illustrated a pre-shrunk plastic rod 56 wherein appropriate blanks 44' can be cut from the rod by conventional means. The heating or pre-annealing technique of FIG. 4 can be applied equally well to rods again reducing the linear dimension by approximately 2% and increasing the circumference by approximately 4%.

Although I have shown and described my invention in what I have conceived to be the most practical and preferred embodiments, it is recognized that departures may be made therefrom within the scope of the claims.

I claim:

1. A method of manufacturing lenses for the eyes comprising:
   heat treating a modified polymerization product of methyl methacrylate, said product being in as-cast form ready for use to make satisfactory lenses prior to heat treating,
   heat treating by placing said product in an oven and heating it to approximately 137.7° C. for about 30 minutes,
   while heating, shrinking said product linearly about 2% and increasing the thickness in another direction about 4%,
   reducing the product temperature to room temperature,
   cutting lens blanks from the treated product in which the optical clarity and wetability has been improved, and
   forming finished lenses from the blanks by conventional grinding means.